United States Patent
Peng et al.

(10) Patent No.: US 12,178,224 B1
(45) Date of Patent: Dec. 31, 2024

(54) USE OF GAMMA-QUATERNARY AMMONIUM BUTYRATE COMPOUND IN PREPARATION OF AN ANIMAL FEED ADDITIVE

(71) Applicant: ANIPHA TECHNOLOGIES PTY LTD, Toorak Gardens (AU)

(72) Inventors: Xianfeng Peng, Guangzhou (CN); Huacheng Huang, Guangzhou (CN)

(73) Assignee: ANIPHA TECHNOLOGIES PTY LTD, Toorak Gardens (AU)

( * ) Notice: Subject to any disclaimer, the term of this patent is extended or adjusted under 35 U.S.C. 154(b) by 0 days.

(21) Appl. No.: 18/235,852

(22) Filed: Aug. 20, 2023

Related U.S. Application Data

(63) Continuation of application No. 17/435,040, filed as application No. PCT/CN2019/077191 on Mar. 6, 2019, now Pat. No. 11,785,966.

(51) Int. Cl.
   *A23K 20/142*   (2016.01)
   *A23K 50/30*    (2016.01)
   *A23K 50/75*    (2016.01)

(52) U.S. Cl.
   CPC ............ *A23K 20/142* (2016.05); *A23K 50/30* (2016.05); *A23K 50/75* (2016.05)

(58) Field of Classification Search
   CPC .................................................. A23K 20/142
   See application file for complete search history.

(56) References Cited

U.S. PATENT DOCUMENTS

| | | | | |
|---|---|---|---|---|
| 5,124,357 A | * | 6/1992 | Newton | A23K 20/142 514/557 |
| 5,498,633 A | * | 3/1996 | Santaniello | C07C 229/22 514/547 |
| 5,525,627 A | * | 6/1996 | Santaniello | A61P 31/04 514/547 |
| 7,977,511 B2 | | 7/2011 | Goel | |
| 8,207,109 B2 | * | 6/2012 | Gaetani | A23L 33/15 424/439 |

FOREIGN PATENT DOCUMENTS

| | | | |
|---|---|---|---|
| CN | 103044278 A | | 4/2013 |
| CN | 105330581 A | | 2/2016 |
| CN | 105968024 A | | 9/2016 |
| CN | 109251157 A | | 1/2019 |
| CN | 110551052 A | | 12/2019 |
| EP | 0375417 A | | 6/1990 |
| EP | 0559625 B1 | * | 8/1993 |
| JP | 1981121441 A | | 9/1981 |
| KR | 20050089387 A | | 9/2005 |
| RU | 2292732 C2 | | 8/2006 |
| WO | 2007003425 A2 | | 1/2007 |

OTHER PUBLICATIONS

International Search Report of PCT/CN2019/077191, dated Nov. 20, 2019.
English Translation of International Search Report of PCT/CN2019/077191.
English Translation of CN103044278A.
Hosein, E. A., "Neuromuscular blocking activity and other pharmacologic properties of various carnitine derivatives," The Journal of Pharmacology and Experimental Therapeutics, vol. 156, p. 565-572, Dec. 9, 1966 (Dec. 9, 1966).
Brendel K., "The resolution of (±)-carnitine and the synthesis of acylcarnitines," Tetrahedron Letters, vol. 31, p. 7323-7326, Aug. 11, 1990 (Aug. 11, 1980).
Bellamy F.D., "A new, short and efficient synthesis of both enantiomers of carnitine," Biochimica Et Biophysica Acta, vol. 137, p. 98-106, Sep. 20, 1966 (Sep. 20, 1996).
Wang Gang, "Combination of L-Carnitine with Lipophilic Linkage-Donating Gemcitabine Derivatives as Intestinal Novel," Journal of Medicinal Chemistry, vol. 60, p. 2552-2561, Feb. 24, 2017 (Feb. 24, 2017).
Katharina Hackl, "Carnitine alkyl ester bromides as novel biosourced ionic liquids, cationic hydrotropes and surfactants," Journal of Colloid and Interface Science, vol. 511, p. 165-173, Sep. 28, 2017 (Sep. 28, 2017).
Dong-liang Lu, "The comparisons in protective mechanisms and efficiencies among dietary a-lipoic acid, b-glucan and Lcarnitine," Fish and Shellfish Immunology, vol. 86, p. 785-793, Dec. 23, 2018 (Dec. 23, 2018).

(Continued)

*Primary Examiner* — Changqing Li
(74) *Attorney, Agent, or Firm* — Kam Wah Law

(57) ABSTRACT

Provided is an application of a γ-quaternary ammonium butyrate compound having formula (I) or a racemate, a stereoisomer, a geometric isomer, a tautomer, a solvate, or a feed-acceptable salt thereof in preparing an animal feed additive, the compound being added to the daily feed of animals at a certain concentration ratio, and being capable of increasing the average daily weight gain of animals under the same food intake conditions, having no significant effect on the daily feed intake of the animals, and reducing the feed-to-meat ratio. The γ-quaternary ammonium butyrate compound disclosed herein can effectively increase the rate of daily weight gain of the animals and improve the growth performance of the animals, having no side effects on the animals, being stable and safe, and improving the production efficiency of the breeding industry whilst ensuring the health of the animals.

Formula (I)

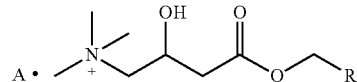

15 Claims, No Drawings

(56) References Cited

OTHER PUBLICATIONS

Xue-jian Liu, "Physiological function and application effect of L-carnitine," Veterinary Pharmaceuticals & Feed Additives, vol. 3, p. 30-31, 1998.
English Translation of Xue-jian Liu, "Physiological function and application effect of L-carnitine," Veterinary Pharmaceuticals & Feed Additives, vol. 3, p. 30-31, 1998.
Bin Yu, "Chemical synthesis of I-carnitine," Chemical Engineer, vol. (3), p. 37-43, 2011.
English Translation of Bin Yu, "Chemical synthesis of I-carnitine," Chemical Engineer, vol. (3), p. 37-43, 2011.
The First Office Action of Patent Family Application JP2021-552644.
English Translation of the First Office Action of Patent Family Application JP2021-552644.
English Translation of KR20050089387A.
The First Office Action of Patent Family Application CA3132384.
Search Report of EP19917768.4.
English translation of CN105968024A.
English translation of CN109251157A.
English translation of JP1981121441A.
English translation of CN105330581A.
English translation of CN110551052A.
English translation of RU2292732C2.

\* cited by examiner

USE OF GAMMA-QUATERNARY AMMONIUM BUTYRATE COMPOUND IN PREPARATION OF AN ANIMAL FEED ADDITIVE

CROSS REFERENCE TO RELATED APPLICATION

This is a continuation application of the U.S. patent application Ser. No. 17/435,040, which is a U.S. national stage application of the International Patent Application No. PCT/CN2019/077191, filed Mar. 6, 2019, both of which are incorporated herein by reference in its entirety.

TECHNICAL FIELD

The present disclosure relates to a field of animal feed additive, in particular to a use of γ-quaternary ammonium butyrate compounds in preparing an animal feed additive or an animal feed.

BACKGROUND OF INVENTION

Carnitine is a kind of amino acids belonging to a quaternary ammonium cation complex, which is an amino acid widely distributed in liver organs, and especially has the highest content in myocardium and skeletal muscle. Most of carnitine components required by body are derived from meats and dairy products in the diet, or are synthesized from two amino acids, lysine and methionine, through biosynthetic methods. Carnitine is a kind of amino acids that promotes the conversion of fat into energy. Red meat is a main source of L-carnitine without toxic side effects. Carnitine has two stereoisomers, including a biologically active L-carnitine and a non-biologically active enantiomer D-carnitine. Studies have been reported that L-carnitine participates in fatty acid R oxidation, promotes fat catabolism, and is capable of eliminating acyl substances in muscle tissue, and protects muscle cells from the destruction of acyl residues, thereby eliminating lactic acids in muscle, and relieving muscle fatigue and cramps. Further studies have been reported that L-carnitine intake can lead to reduced body fat and weight without reducing water and muscle. In 2003, L-carnitine was recognized by the International Obesity Health Organization as the safest weight loss nutritional supplement without side effects.

L-carnitine is widely used in animal breeding industry, and is mainly used to reduce fat content of animal meats, reduce weight or prevent animal liver and gall diseases. Research results showed that a puffed food for dog supplemented with L-carnitine can effectively reduce the fat of obese dogs and ensure their health. Other research results showed that bile acids and L-carnitine play an important role in fat metabolism and can effectively prevent nutritional liver and gall diseases in farm animals. Another research result showed that betaine and saccharicterpenin can be used to synergistically promote L-carnitine tartrate to promote the oxidation and decomposition of fat in the chicken body and increase lean meat percentage. There are also research results showing that addition of carnitine in the diet of cattle or sheep can effectively combat ammonia toxicity caused by high-level protein. In the field of human medicine, carnitine is a commonly used hypolipidemic drug for hemodialysis patients. Although many studies have shown that carnitine has biological effects in the breeding of ruminants, such as beef cattle or sheep, at various growth stages, impacts on milk production and growth performance are almost always disappointing. On Dec. 13, 2018, Dong-Liang Lu studied impacts of L-carnitine on the production performance of tilapia. Compared with the blank Control group, the weight gain rate of tilapia supplemented with L-carnitine in basal diet in the Experimental group was reduced by 1.2%.

Carnitine itself is a quaternary ammonium cation complex, which is usually hygroscopic. In the 1970s, studies found that fatty ester derivatives of the carboxyl group of Carnitine was a chemical substance that is physically and chemically stable and does not absorb moisture. Such carnitine derivatives are used as preparation intermediates in the chemical industry as a protection scheme for the carboxyl group in the preparation of carnitine or prodrugs formed by combining carnitine as a drug ligand with drugs. These carnitine derivatives can also be used as surfactants in cosmetics, food or medicine field.

Feed additives refer to small or trace substances added during processing, production, and use of feeds, including nutritive feed additives and general feed additives. General feed additives refer to small or trace amounts of substances mixed into feeds to ensure or improve the feed quality and increase the efficiency of feed utilization. At present, the general feed additives commonly used that can efficiently and stably increase the efficiency of feed utilization and improve the animal production performance mainly include high-level copper agents, high-level zinc agents, feed antibiotics, chemically synthesized antimicrobial agents, etc. However, the long-term use of these substances in the breeding industry has great side effects, such as the disadvantages of liver and kidney toxicity to animals, growth inhibition, kidney function damage, urinary tract disorders, teratogenicity, mutagenesis, the production of drug resistance, drug residues and environmental pollution, or the like. In order to protect the health of animals and improve the production efficiency of the breeding industry, it is necessary to develop a new effective, stable and safe feed additive being capable of improving animal production performance.

SUMMARY OF INVENTION

In view of the above, an object of the present disclosure is to provide a use of a γ-quaternary ammonium butyrate compound, or a racemate, a stereoisomer, a geometric isomer, a tautomer, a solvate or a feed acceptable salt thereof in preparing an animal feed additive or an animal feed, wherein the γ-quaternary ammonium butyrate compound can improve the production performance of farm animals.

To achieve the above-mentioned object, the present disclosure provides a use of a γ-quaternary ammonium butyrate compound having Formula (I), or a racemate, a stereoisomer, a geometric isomer, a tautomer, a solvate or a feed acceptable salt thereof in preparing an animal feed additive,

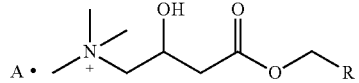

Formula (I)

wherein, A is an anion; R is $C_1$-$C_{20}$ alkyl, or $C_1$-$C_{20}$ alkyl substituted with one, two, three, four, or five $R^3$, or $C_6$-$C_{12}$ aryl, or $C_4$-$C_{12}$ heteroaryl, or ($C_1$-$C_4$ alkylene)-$C_6$-$C_{12}$ aryl, or ($C_1$-$C_4$ alkylene)-$C_4$-$C_{12}$ heteroaryl, wherein each of $C_6$-$C_{12}$ aryl, $C_4$-$C_{12}$ heteroaryl, ($C_1$-$C_4$ alkylene)-C$_6$-C$_{12}$ aryl and (C$_1$-C$_4$ alkylene)-C$_4$-C$_{12}$ heteroaryl, is optionally substituted with one, two, three, four, or five R$^4$; and R$^3$ is —OH, —NH$_2$, —CN, —SH or X$_1$, wherein X$_1$ is F, Cl, Br or I; and R$^4$ is —OH, —NH$_2$, —NO$_2$, —CN, —SH, —X$_2$, C$_1$-C$_5$ alkoxy, C$_1$-C$_5$ alkyl, or C$_1$-C$_5$ alkyl substituted with X$_2$, wherein X$_2$ is F, Cl, Br or I.

The present disclosure further provides a feed composition comprising at least one of the γ-quaternary ammonium butyrate compound, or the racemate, the stereoisomer, the geometric isomer, the tautomer, the solvate or the feed acceptable salt thereof as described above as a main component.

The present disclosure further provides a use of the feed composition described above in preparing an animal feed or an animal feed additive.

Based on the above-mentioned technical solutions, the present disclosure has the following effects.

The present disclosure provides a use of the γ-quaternary ammonium butyrate compound having Formula (I), or a racemate, a stereoisomer, a geometric isomer, a tautomer, a solvate, or a feed acceptable salt thereof in preparing an animal feed additive. The compound is added to the daily feed of animals at a certain concentration ratio so as to increase the average daily weight gain of animals under the same food intake conditions, without no significant effects on the daily feed intake of the animals, thereby reducing the feed conversion ratio. It can been seen that, the γ-quaternary ammonium butyrate compound or the racemate, the stereoisomer, the geometric isomer, the tautomer, the solvate, or the feed acceptable salt thereof according to the present disclosure can effectively increase the daily weight gain rate of animals and improve the growth performance of animals, which has no side effects on animals, and is stable and safe, and improves the production efficiency of the breeding industry while ensuring the health of animals.

DETAILED DESCRIPTION OF THE EMBODIMENTS

In order to facilitate the understanding of the present disclosure, the present disclosure will be described more fully hereinafter with reference to the embodiments, preferred embodiments of the present disclosure are given below. However, the present disclosure may be implemented in many different forms and is not limited to the embodiments described herein. These embodiments are provided to make the understanding of the disclosure of the present disclosure more thorough and complete. It should be understood that the experimental methods for which specific conditions are not indicated in the following embodiments are usually performed in accordance with conventional conditions or in accordance with the conditions recommended by the manufacturer. Various common reagents used in the embodiments are all commercially available products.

Unless otherwise defined, all technical and scientific terms used herein have the same meaning as commonly understood by skilled person in the art to which the present disclosure belongs. The terms used in the specification of the present disclosure are for the purpose of describing specific embodiments only and are not intended to limit the present disclosure. The term "and/or" used herein includes any and all combinations of one or more of the associated listed items.

Certain embodiments of the present disclosure will be described in detail herein, the examples of which are illustrated by the accompanying structural formulas and chemical formulas. The present disclosure is intended to cover all substituted, modified and equivalent technical solutions, which are all included in the scope of the present disclosure as defined by the claims. In addition, certain technical features of the present disclosure are described separately in multiple independent embodiments for clarity, but they can also be provided in combination or in any suitable subcombination in a single example.

Compounds

The present disclosure relates to a use of a γ-quaternary ammonium butyrate compound having Formula (I), or a racemate, a stereoisomer, a geometric isomer, a tautomer, a solvate or a feed acceptable salt thereof in preparing an animal feed additive, Formula (I)

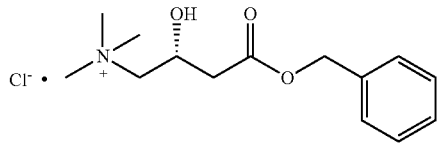

wherein, A is an anion, and a relationship between the anion and the cation shown in Formula (I) only means that the compound is an ionic compound, and does not mean that a sum of positive and negative charges of ions is equal.

R is a substituted or unsubstituted C$_1$-C$_{20}$ alkyl, wherein the C$_1$-C$_{20}$ alkyl is optionally substituted with one, two, three, four, or five R$^3$, and wherein R$^3$ is —OH, —NH$_2$, —CN, —SH or X$_1$, wherein X$_1$ is F, Cl, Br or I; or R is a substituted or unsubstituted C$_6$-C$_{12}$ aryl, C$_4$-C$_{12}$ heteroaryl, (C$_1$-C$_4$ alkylene)-C$_6$-C$_{12}$ aryl, (C$_1$-C$_4$ alkylene)-C$_4$-C$_{12}$ heteroaryl, wherein each of the C$_6$-C$_{12}$ aryl, C$_4$-C$_{12}$ heteroaryl, (C$_1$-C$_4$ alkylene)-C$_6$-C$_{12}$ aryl and (C$_1$-C$_4$ alkylene)-C$_4$-C$_{12}$ heteroaryl, is optionally substituted with one, two, three, four, or five R$^4$, and wherein R$^4$ is —OH, —NH$_2$, —NO$_2$, —CN, —SH, —X$_2$, C$_1$-C$_5$ alkoxy, C$_1$-C$_5$ alkyl, or C$_1$-C$_5$ alkyl substituted with X$_2$, wherein X$_2$ is F, Cl, Br or I.

Generally, "substituted" means that one or more of the hydrogen atoms that can be substituted in the given structure are substituted by specific substituents. A substituted group may be formed by the substitution of one substituent group at each substitutable position of the group. When more than one position in the given structural formula can be substituted by one or more specific substituents, it may be same or differently substituted by the substituent groups at each position.

In the present disclosure, "C$_a$-C$_b$ alkyl" means a linear or branched saturated alkyl containing a to b carbon atoms, such as, methyl, ethyl, propyl, isopropyl, etc. For example, "C$_1$-C$_5$ alkyl" means a linear or branched saturated alkyl containing 1 to 5 carbon atoms. "C$_3$-C$_7$ cycloalkyl" means a cyclic alkyl containing 3 to 7 carbon atoms that has only two elements of carbon and hydrogen, such as, cyclopropyl, 2-methylcyclopropyl, cyclopentyl, etc. "C$_1$-C$_5$ alkoxy" means a group containing 1 to 5 carbon atoms and one oxygen atom, such as, methoxy, ethoxy, propoxy, isopropoxy, etc. "C$_6$-C$_{12}$ aryl" means a cyclic group containing 6 to 12 carbon atoms with aromaticity, such as, a benzene ring, etc. "C$_4$-C$_{12}$ heteroaryl" means an cyclic group containing 4 to 12 carbon atoms and at least one heteroatom (including but being not limited to oxygen atom (O), sulfur atom (S), nitrogen atom (N)) with aromaticity, such as, pyrrolidinyl, pyridinyl, etc. "$C_n$-$C_m$ alkylene" means an alkyl containing n to m methylene groups, such as, $CH_2$, $(CH_2)_2$, and the like.

In some embodiments, R in the γ-quaternary ammonium butyrate compound having Formula (I) is a substituted or an unsubstituted $C_6$-$C_{12}$ aryl.

In further embodiments, the unsubstituted $C_6$-$C_{12}$ aryl includes but is not limited to phenyl or naphthyl.

In some embodiments, R is

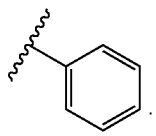

In addition, wherein R is $C_6$-$C_{12}$ aryl, optionally substituted with one, two, three, four, or five $R^4$, and $R^4$ is —OH, —$NH_2$, —$NO_2$, —CN, —SH, —$X_2$, $C_1$-$C_5$ alkoxy, $C_1$-$C_5$ alkyl, or $C_1$-$C_5$ alkyl substituted with $X_2$, wherein $X_2$ is F, Cl, Br or I.

In further embodiments, the $C_6$-$C_{12}$ aryl is preferably a substituted phenyl.

Specifically, the substituted phenyl is optionally substituted with one, two, three, four, or five $R^4$, and $R^4$ is —OH, —$NH_2$, —$NO_2$, —CN, —SH, —$X_2$, $C_1$-$C_5$ alkoxy, $C_1$-$C_5$ alkyl, or $C_1$-$C_5$ alkyl substituted with $X_2$, wherein $X_2$ is F, Cl, Br or I.

In some embodiments, R is selected from the group consisting of

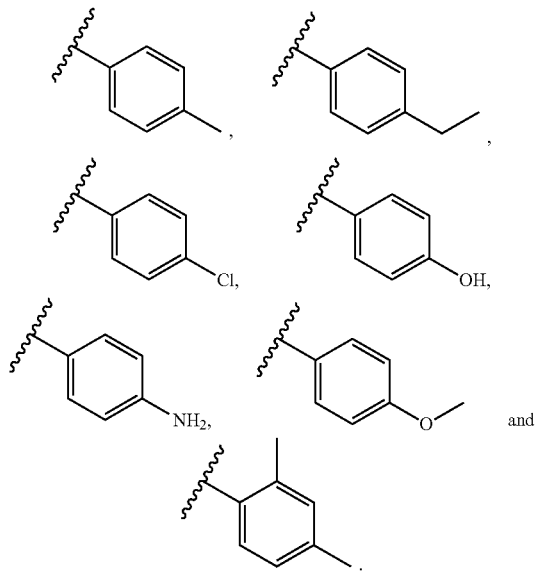

In some embodiments, R in the γ-quaternary ammonium butyrate compound having Formula (I) is a substituted or unsubstituted ($C_1$-$C_4$ alkylene)-$C_6$-$C_{12}$ aryl.

In further embodiments, when R is an unsubstituted ($C_1$-$C_4$ alkylene)-$C_6$-$C_{12}$ aryl, wherein the $C_6$-$C_{12}$ aryl includes but is not limited to phenyl or naphthyl, and the alkylene is preferably methylene.

In some embodiments, R is

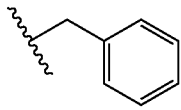 [SMILES: *Cc1ccccc1]

(benzyl).

In addition, when R is a substituted —($C_1$-$C_4$ alkylene)-$C_6$-$C_{12}$ aryl, wherein the $C_6$-$C_{12}$ aryl is a $C_6$-$C_{12}$ aryl optionally substituted with one, two, three, four, or five $R^4$, and $R^4$ is —OH, —$NH_2$, —$NO_2$, —CN, —SH, —$X_2$, $C_1$-$C_5$ alkoxy, $C_1$-$C_5$ alkyl, or $C_1$-$C_5$ alkyl substituted with $X_2$, wherein $X_2$ is F, Cl, Br or I.

In further embodiments, the $C_6$-$C_{12}$ aryl is preferably $C_6$ aryl.

Specifically, R is a benzyl optionally substituted with one, two, three, four, or five $R^4$, and $R^4$ is —OH, —$NH_2$, —$NO_2$, —CN, —SH, —$X_2$, $C_1$-$C_5$ alkoxy, $C_1$-$C_5$ alkyl, or $C_1$-$C_5$ alkyl substituted with $X_2$, wherein $X_2$ is F, Cl, Br or I.

In some embodiments, R is selected from the group consisting of

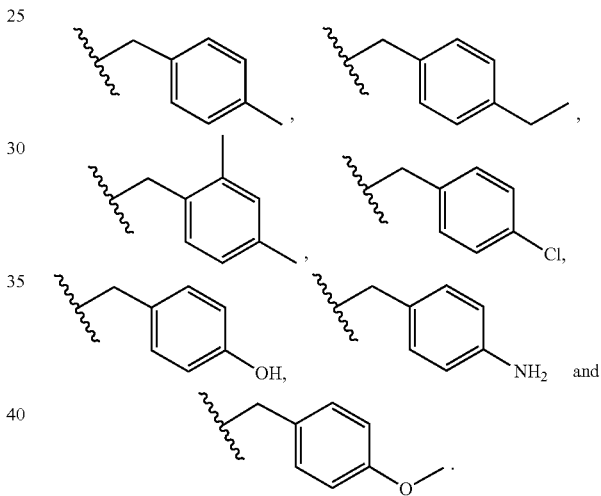

In some embodiments, R in the γ-quaternary ammonium butyrate compound having Formula (I) is a substituted or unsubstituted $C_4$-$C_{12}$ heteroaryl.

In further embodiments, when R is an unsubstituted $C_4$-$C_{12}$ heteroaryl, wherein the $C_4$-$C_{12}$ heteroaryl includes but is not limited to pyrrolidinyl, pyrazolyl or pyridyl.

In some embodiments, R is selected from the group consisting of

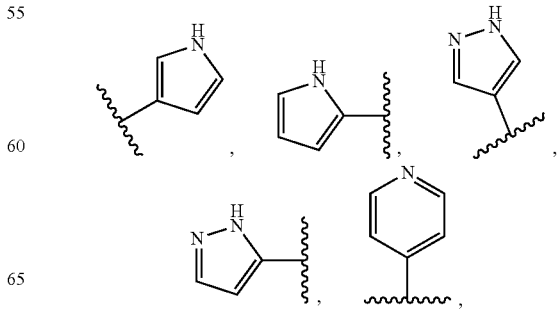

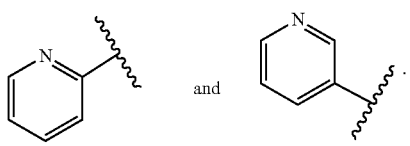

In addition, when R is a substituted $C_4$-$C_{12}$ heteroaryl, wherein the $C_4$-$C_{12}$ heteroaryl is optionally substituted with one, two, three, four, or five $R^4$, and $R^4$ is —OH, —NH$_2$, —NO$_2$, —CN, —SH, —X$_2$, $C_1$-$C_5$ alkoxy, $C_1$-$C_5$ alkyl, or $C_1$-$C_5$ alkyl substituted with X$_2$, wherein X$_2$ is F, Cl, Br or I.

In further embodiments, the $C_4$-$C_{12}$ heteroaryl is preferably pyrrolidinyl, pyrazolyl or pyridyl.

In some embodiments, the $C_4$-$C_{12}$ heteroaryl is selected from the group consisting of

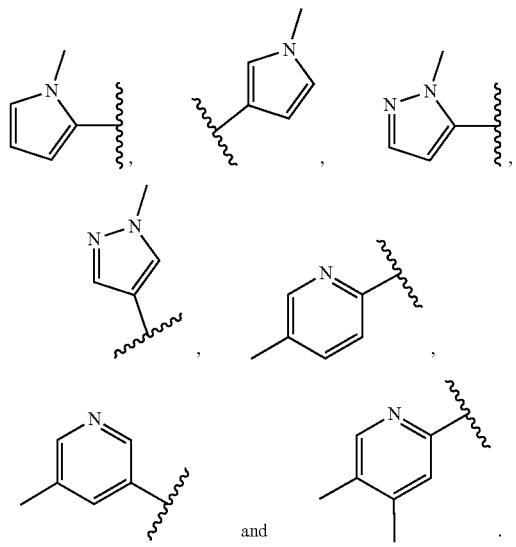

In some embodiments, R in the γ-quaternary ammonium butyrate compound having Formula (I) is a substituted or unsubstituted ($C_1$-$C_4$ alkylene)-$C_4$-$C_{12}$ heteroaryl.

In further embodiments, the $C_4$-$C_{12}$ heteroaryl is an unsubstituted ($C_1$-$C_4$ alkylene)-$C_4$-$C_{12}$ heteroaryl, wherein the $C_4$-$C_{12}$ heteroaryl includes but is not limited to pyrrolidinyl, pyrazolyl or pyridyl, and the $C_1$-$C_4$ alkylene is preferably methylene.

In some embodiments, R is selected from the group consisting of

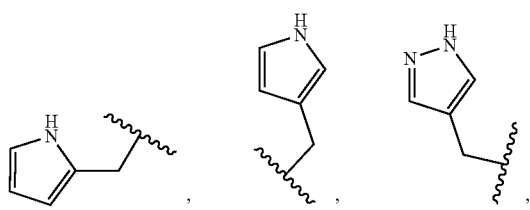

In addition, when R is a substituted ($C_1$-$C_4$ alkylene)-$C_4$-$C_{12}$ heteroaryl, wherein the $C_4$-$C_{12}$ heteroaryl is optionally substituted with one, two, three, four, or five $R^4$, and $R^4$ is —OH, —NH$_2$, —NO$_2$, —CN, —SH, —X$_2$, $C_1$-$C_5$ alkoxy, $C_1$-$C_5$ alkyl, or $C_1$-$C_5$ alkyl substituted with X$_2$, wherein X$_2$ is F, Cl, Br or I.

In further embodiments, the $C_4$-$C_{12}$ heteroaryl is preferably pyrrolidinyl, pyrazolyl or pyridyl, and the $C_1$-$C_4$ alkylene is preferably methylene.

In some embodiments, R is selected from the group consisting of

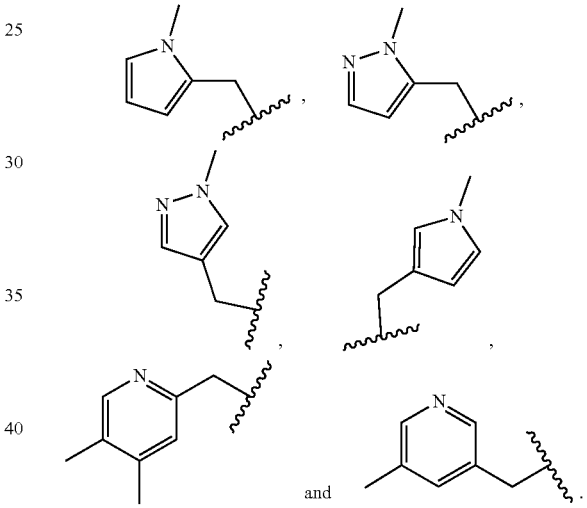

In some embodiments, R in the γ-quaternary ammonium butyrate compound having Formula (I) is a substituted or unsubstituted $C_1$-$C_{20}$ alkyl; when R is a substituted $C_1$-$C_{20}$ alkyl, the substituted $C_1$-$C_{20}$ alkyl is a $C_1$-$C_{20}$ alkyl optionally substituted with one, two, three, four, or five $R^3$, and $R^3$ is —OH, —NH$_2$, —CN, —SH or X$_1$, wherein X$_1$ is F, Cl, Br or I;

Optionally, R is preferably a linear $C_1$-$C_{20}$ alkyl.

In further embodiments, R is preferably a linear $C_1$-$C_{11}$ alkyl.

Specifically, the linear $C_1$-$C_{11}$ alkyl is selected from the group consisting of: methyl, ethyl, n-propyl, n-butyl, n-pentyl, n-hexyl, n-heptyl, n-octyl, n-nonyl, n-decyl and n-undecyl.

In some embodiments, R is methyl.

In other embodiments, R is ethyl.

In other embodiments, R is n-propyl.

Optionally, R is a branched $C_1$-$C_{20}$ alkyl.

In some embodiments, R is preferably isopropyl or tert-butyl.

In some embodiments, the anion A is a negative monovalent anion.

Optionally, the negative monovalent anion includes, but is not limited to, chloride, bromide, iodide or perchlorate ions.

In some embodiments, the anion A is a negative divalent anion.

Optionally, the negative divalent anion includes, but is not limited to, sulfate ion or carbonate ion.

In some embodiments, the anion A is an organic acid ion.

Optionally, the organic acid ion includes, but is not limited to, acetate ion, fumarate ion, maleate ion, and the like.

In some specific embodiments, the γ-quaternary ammonium butyrate compound of the present disclosure includes one of the following structures and the corresponding racemates, stereoisomers, geometric isomers, tautomers, solvates, and feed acceptable salts of the above-mentioned compounds:

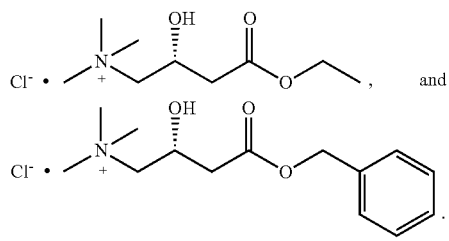
and
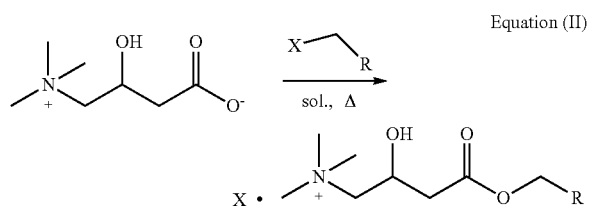

Preparation and Purification of Compounds

The preparation method of the γ-quaternary ammonium butyrate compound having Formula (I) of the present disclosure is as shown in Equation (II), wherein, Carnitine is used as a starting material, and the main reaction involved is a substitution reaction.

Equation (II)

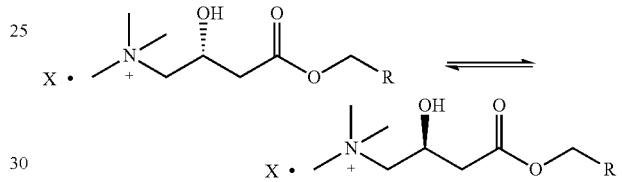

To be clear, "sol." in Equation (II) represents a reaction solvent, and "Δ" represents heating.

In some embodiments, the γ-quaternary ammonium butyrate compound is a chiral compound, which is prepared from Carnitine with a chiral structure (as shown in Formula (III)) or a racemate thereof. The γ-quaternary ammonium butyrate compound of the present disclosure is selected from stereoisomers, such as laevoisomer L-(−)-γ-quaternary ammonium butyrate compound (structure is represented by Formula (IV)), dextroisomer D-(+)-γ-quaternary ammonium butyrate compound (structure is represented by Formula (V)), racemate DL-(±)-γ-quaternary ammonium butyrate compound and the like.

Formula (III)

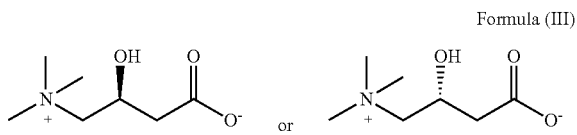

Formula (IV)

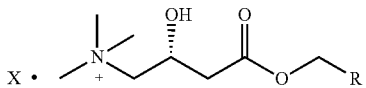

Formula (V)

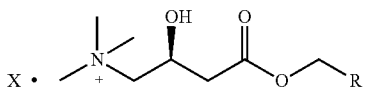

In some embodiments, the chiral stereoisomers of the γ-quaternary ammonium butyrate compound can perform a transformation of stereoconfiguration under suitable conditions, for example, the stereoconfiguration of the γ-quaternary ammonium butyrate compound is interconverted to form a tautomer, and the interconversion process is shown in Equation (VI).

Equation (VI)

When the corresponding γ-quaternary ammonium butyrate compound generated from the reaction of involved reactants has a rigid structure, the reaction substrate can generate different geometric isomer products during the reaction.

The aforementioned stereoisomer, geometric isomer and tautomer are also included in the scope of implementation of the present disclosure.

The "stereoisomer" involved in the present disclosure refers to a compound having the same chemical structure but different arrangement of atoms or groups in space, including an enantiomer, a diastereomer, a conformational isomer, a geometric isomer, and an atropisomer, and the like. The "enantiomer" refers to two isomers of a compound that cannot be overlapped but are mirror images of each other. The "diastereomer" refers to a stereoisomer that has two or more chiral centers and its molecules are not mirror images of each other, and has different physical properties, such as melting point, boiling point, spectral property, and reactivity. Diastereoisomer mixtures can be separated by high-resolution analysis operations such as electrophoresis or chromatography. The "tautomer" refers to constitutional isomers having different energies that can be converted into each other through a low energy barrier.

In some embodiments, the preparation process of the γ-quaternary ammonium butyrate compound provided in the present disclosure also involves a separation, purification or recrystallization process of the reaction products. The reaction products can be obtained as crude products from the reaction system by a solvent removal method. In order to obtain solid substances with higher chemical purity and lower impurity content, the crude products are dissolved, crystallized or precipitated or recrystallized and separated in alcohol solvent, alcohol-water mixed solvent or other organic solvents that can be used for product recrystallization under suitable temperature, light and mechanical vibration conditions, to obtain a γ-quaternary ammonium butyrate compound with certain crystal state. The γ-quaternary ammonium butyrate compound with certain crystal state is a crystal of the γ-quaternary ammonium butyrate compound or a solvate of the γ-quaternary ammonium butyrate compound. The solvate of the γ-quaternary ammonium butyrate compound may be selected from hydrates of the γ-quaternary ammonium butyrate compound or ethanol solvates of the γ-quaternary ammonium butyrate compound.

The "solvate" involved in the present disclosure refers to an eutectic association compound formed by binding chemically equivalent or non-chemically equivalent solvent molecules to the compound of the present disclosure through non-covalent intermolecular forces under external conditions and internal conditions during the contact between the compound of the present disclosure and the solvent molecules. Solvents for forming solvates include, but are not limited to, solvents such as water, acetone, ethanol, methanol, dimethyl sulfoxide, ethyl acetate, acetic acid, and isopropanol, or the like. The "hydrate" refers to an association compound or crystal formed when the solvent molecule is water, i.e., a compound formed by binding the chemically equivalent or non-chemically equivalent water through the non-covalent intermolecular forces.

In order to obtain solid substances with higher chemical purity and lower impurity content, the preparation of the γ-quaternary ammonium butyrate compound provided by the present disclosure may further involve a post-treatment by salting out method. The salting out method is a salt precipitation process of the γ-quaternary ammonium butyrate compound and corresponding organic base, inorganic base, organic acid or inorganic acid using the principle of acid-base neutralization method, acid-base coordination method or acid-base chelation method, to obtain feed acceptable salts. The inorganic acid includes, but is not limited to, hydrochloric acid, hydrobromic acid, phosphoric acid, sulfuric acid, nitric acid or a combination thereof. The organic base includes, but is not limited to, ammonia or triethylamine. The inorganic base includes, but is not limited to, sodium hydroxide, potassium hydroxide, magnesium hydroxide, or calcium hydroxide.

The feed acceptable salts are salts formed by the γ-quaternary ammonium butyrate compound of the present disclosure and organic base, inorganic base, organic acid or inorganic acid that are non-toxic to animals. The "feed acceptable" means that the substance or composition must be chemically or toxicologically suitable, which is related to the feed to be formed or the farm animals eating it.

In some embodiments, the γ-quaternary ammonium butyrate compound of the present disclosure is an ionic compound, which forms a acid-base coordination salt and/or acid-base chelate salt with an inorganic acid or an organic acid in the salting-out precipitation process of post-treatment. The organic acid includes, but is not limited to, acetic acid, maleic acid, succinic acid, mandelic acid, fumaric acid, malonic acid, malic acid, 2-hydroxypropionic acid, pyruvic acid, oxalic acid, glycolic acid, salicylic acid, glucuronic acid, galactitol acid, citric acid, tartaric acid, aspartic acid, glutamic acid, benzoic acid, p-methylbenzoic acid, cinnamic acid, p-toluenesulfonic acid, benzenesulfonic acid, methanesulfonic acid, ethanesulfonic acid, triflic acid, or a combination thereof. The inorganic acid includes, but is not limited to, sulfuric acid, hydrochloric acid, hydrobromic acid, hydroiodic acid, phosphoric acid, and the like.

Use of the γ-Quaternary Ammonium Butyrate Compound Involved in the Present Disclosure The γ-quaternary ammonium butyrate compound and the racemate, the stereoisomer, the geometric isomer, the tautomer, the solvate or the feed acceptable salt thereof are used in preparing an animal feed additive.

The "animal" involved in the present disclosure refers to humans or farm animals who cannot synthesize inorganic substances into organic substances, and can only use organic substances as foodstuff for life activities such as ingestion, digestion, absorption, respiration, circulation, excretion, sensation, movement, and breeding. The "farm animals" includes poultry, livestock, aquaculture animals and other animals that are artificial feeding and legally captured, including pets, such as cats and dogs. The term "livestock" refers to any one of, for example, a pig, cattle, horse, goat, sheep, deer and many useful rodents. The term "poultry" includes, for example, a chicken, duck, goose, quail, pigeon and the like. The term "aquaculture animals" includes, for example, a fish, shrimp, turtle, amyda and the like.

The γ-quaternary ammonium butyrate compound and the racemate, the stereoisomer, the geometric isomer, the tautomer, the solvate or the feed acceptable salt thereof provided by the present disclosure are used to prepare non-nutritive additives for improving production performance of animals at various growth stages. The animals may be selected from livestock, poultry, aquaculture animals or pets at various growth stages.

Furthermore, the livestock includes, but is not limited to a pig, cattle, sheep, horse, rabbit, mink or donkey, the poultry includes, but is not limited to a chicken, turkey, duck, goose, quail or pigeon, and the aquaculture animals include, but are not limited to a fish, shrimp, turtle, crab, amyda, bullfrog, eel or loach, and the pets include, but are not limited to a dog or cat of various subspecies.

In one embodiment, the γ-quaternary ammonium butyrate compound and the racemate, the stereoisomer, the geometric isomer, the tautomer, the solvate or the feed acceptable salt thereof provided by the present disclosure are used to prepare a feed additive for improving the production performance of porkers, which have an improvement effect on the average daily gain or feed conversion efficiency of porkers.

In another embodiment, the γ-quaternary ammonium butyrate compound and the racemate, the stereoisomer, the geometric isomer, the tautomer, the solvate or the feed acceptable salt thereof provided by the present disclosure are used to prepare a feed additive capable of significantly improving the production performance of broilers or layers.

Feed Composition Involved in the Present Disclosure

A feed composition comprises at least one of the γ-quaternary ammonium butyrate compound and the racemate, the stereoisomer, the geometric isomer, the tautomer, the solvate or the feed acceptable salt thereof, and a feedable accessory. The feedable accessory is a carrier, a diluent, an excipient, and a solvent that are feedable, or combinations thereof.

The "feed" involved in the present disclosure refers to an industrially processed and manufactured product for animal consumption.

The "composition" involved in the present disclosure refers to a compound collective comprising one or more compounds as effective ingredients.

The "comprising" mentioned in the present disclosure is an open-type expression, which includes the contents explicitly indicated in the present disclosure, but does not exclude other contents.

The "carrier" involved in the present disclosure refers to a feedable substance capable of carrying active ingredients, improving its dispersibility, and having good chemical stability and adsorption, including an organic carrier and an inorganic carrier. The organic carrier is a material containing a lot of crude fiber, including but not being limited to corn flour, corncob flour, wheat bran, rice hull flour, defatted rice bran, rice bran and hull, corn stalk flour, peanut husk flour, and the like. The inorganic carrier is a mineral, mainly divided into calcium salts and silicon oxides, which is used for the production of trace element premix, including but not limited to calcium carbonate, silicate, vermiculite, zeolite, sepiolite, and the like.

The "diluent" involved in the present disclosure refers to a substance that evenly distributes the additive raw materials in the material, dilutes the high-concentration additive raw materials into a low-concentration premixing agent or premix, which can separate trace components from each other and reduce the interreaction between the active ingredients so as to increase the stability of the active ingredients without affecting the physical and chemical properties of related substances, including an organic diluent or an inorganic diluent. The organic diluent includes, but is not limited to, corn flour, degerminated corn flour, dextrose (glucose), sucrose, manna-croup with bran, fried soybean flour, middling flour, corn gluten meal, and the like. The inorganic diluent includes, but is not limited to, limestone, calcium dihydrogen phosphate, shell powder, kaolin (porcellanite), table salt and sodium sulfate.

The excipient is a wetting agent that induces the inherent viscosity of a substance, a binder that binds substances together, a disintegrant that breaks the entire sheet of a substance into many fine particles, a retention aid that reduces friction between particles or an antiblock agent that prevents material adhesion, including, but being not limited to, magnesium stearate, talc, vegetable oil, magnesium lauryl sulfate, starch, starch slurry, water, inorganic salt, dextrin, powdered sugar, and the like.

The "solvent" involved in the present disclosure refers to a solvent required to dissolve or disperse solids, including, but being not limited to, water, ethanol, glycerin, and the like.

In some embodiments, the feed composition further comprises an additional animal feed additive and/or an animal feed material.

The animal feed additive is a nutritive feed additive, a general feed additive or a medicated feed additive.

The nutritive feed additive refers to a small or trace substance that is added to compound feeds to balance feed nutrients, improve feed utilization, and directly exert nutritional effects on animals, including an amino acid, an amino acid salt and analogs thereof, a vitamin and vitamins, a mineral element and complexes (chelates) thereof, a microbial enzyme preparation or a non-protein nitrogen.

The general feed additive is also called non-nutritive additive, which refers to some non-nutritive substances that are added to feed to improve feed utilization, ensure the quality of feed, and are beneficial to the health or metabolism of animals, including growth promoter, insect repellent and health care agent, flavoring and attractant agent, feed texturizer, feed modulator, feed storage agent and Chinese herbal medicine additive.

More specifically, the non-nutritive additive is a growth promoter, including, but being not limited to, butyric acid, calcium butyrate, sodium butyrate, tannic acid, p-thymol, p-thymol ester, p-thymol salt, 2-hydroxybenzoic acid, β-acid, β-acid ester, β-acid salt, hexahydro-β-acid, hexahydro-β-acid ester, hexahydro-β-acid salt, benzoic acid or calcium benzoate, zinc oxide, zinc sulfate, and zinc chloride.

In one embodiment, the non-nutritive additive is calcium butyrate.

In another embodiment, the non-nutritive additive is tannic acid.

The medicated feed additive includes, but is not limited to, premixed materials for veterinary drugs that have the functions of preventing animal diseases and promoting animal growth and can be added to feed for a long time and be incorporated with carriers or diluents.

Specifically, the medicated feed additive is a feed antibiotic including, but being not limited to, polymyxin, salinomycin, avilamycin, bacitracin, virginiamycin, nosiheptide, flavomycin, enramycin, kitasamycin, olaquindox, oxytetracycline or aureomycin.

In some embodiment, the composition comprising the γ-quaternary ammonium butyrate compound and the racemate, the stereoisomer, the geometric isomer, the tautomer, the solvate or the feed acceptable salt thereof further includes one or more of a nutritive feed additive, a general feed additive and a medicated feed additive.

In some embodiment, the animal feed material is a feed substance such as grains and processed products thereof, oil seeds and processed products thereof, seeds of legumes and processed products thereof, tubers, tuberous roots and processed products thereof, other seeds and fruit products and processed products thereof, forage grass, coarse fodder and processed products thereof, other plants, algae and processed products thereof, dairy products and by-products thereof, terrestrial animal products and by-products thereof, fishes, other aquatic organisms and by-products thereof, minerals, microbial fermentation products and by-products, and other feedstuffs, or the like.

Use of the Feed Composition

The present disclosure relates to a use of the above-mentioned feed composition comprising the γ-quaternary ammonium butyrate compound and the racemate, the stereoisomer, the geometric isomer, the tautomer, the solvate or the feed acceptable salt thereof.

In some embodiments, the above-mentioned feed composition comprising the γ-quaternary ammonium butyrate compound and the racemate, the stereoisomer, the geometric isomer, the tautomer, the solvate or the feed acceptable salt thereof is used in preparing an animal feed additive.

The animal feed additives prepared by using the feed composition comprising the γ-quaternary ammonium butyrate compound and the racemate, the stereoisomer, the geometric isomer, the tautomer, the solvate or the feed acceptable salt thereof are livestock feed additives, poultry feed additives, aquaculture animal feed additives or pet feed additives.

Specifically, the feed composition comprising the γ-quaternary ammonium butyrate compound and the racemate, the stereoisomer, the geometric isomer, the tautomer, the solvate or the feed acceptable salt thereof is used to prepare the livestock feed additives. The livestock includes, but is not limited to, a pig, cattle, sheep, horse, rabbit, mink, and the like at various growth stages.

Specifically, the feed composition comprising the γ-quaternary ammonium butyrate compound and the racemate, the stereoisomer, the geometric isomer, the tautomer, the solvate or the feed acceptable salt thereof is used to prepare the poultry feed additives. The poultry includes, but is not limited to, a chicken, duck, goose, pigeon, and the like at various growth stages.

Specifically, the feed composition comprising the γ-quaternary ammonium butyrate compound and the racemate, the stereoisomer, the geometric isomer, the tautomer, the solvate or the feed acceptable salt thereof is used to prepare the pet feed additives. The pet includes, but is not limited to, an artificial feeding dog or cat.

In some embodiments, the animal feed additives prepared with the composition comprising the γ-quaternary ammonium butyrate compound and the racemate, the stereoisomer, the geometric isomer, the tautomer, the solvate or the feed acceptable salt thereof are premixing agents, multi-premixing agents, water aquas or granules.

In some embodiments, the above-mentioned feed composition comprising the γ-quaternary ammonium butyrate compound and the racemate, the stereoisomer, the geometric isomer, the tautomer, the solvate or the feed acceptable salt thereof is used in the preparation of animal feeds.

The animal feeds prepared by using the feed composition comprising the γ-quaternary ammonium butyrate compound and the racemate, the stereoisomer, the geometric isomer, the tautomer, the solvate or the feed acceptable salt thereof are livestock feeds, poultry feeds, aquaculture animal feeds or pet feeds.

Specifically, the feed composition comprising the γ-quaternary ammonium butyrate compound and the racemate, the stereoisomer, the geometric isomer, the tautomer, the solvate or the feed acceptable salt thereof is used to prepare the livestock feeds. The livestock includes, but is not limited to, a pig, cattle, sheep, horse, rabbit, mink, and the like at various growth stages.

Specifically, the feed composition comprising the γ-quaternary ammonium butyrate compound and the racemate, the stereoisomer, the geometric isomer, the tautomer, the solvate or the feed acceptable salt thereof is used to prepare the poultry feeds. The poultry includes, but is not limited to, a chicken, duck, goose, pigeon, and the like at various growth stages.

Specifically, the feed composition comprising the γ-quaternary ammonium butyrate compound and the racemate, the stereoisomer, the geometric isomer, the tautomer, the solvate or the feed acceptable salt thereof is used to prepare the pet feeds. The pet includes, but is not limited to, an artificial feeding dog or cat.

In some embodiments, the feeds prepared by using the feed composition comprising the γ-quaternary ammonium butyrate compound and the racemate, the stereoisomer, the geometric isomer, the tautomer, the solvate or the feed acceptable salt thereof are single feeds, concentrated feeds, formula feeds, multi-premixes or concentrate supplements.

Specifically, the compound feed is a complete formula feed.

Method for Improving the Production Performance of Farm Animals.

In some feeding embodiments, the farmer feeds animals with the feed additives comprising the γ-quaternary ammonium butyrate compound and the racemate, the stereoisomer, the geometric isomer, the tautomer, the solvate or the feed acceptable salt thereof along with feeds, which can significantly improve the production performance of the animals.

In some embodiments, the feed additives are premixing agents, multi-premixing agents, granules or water aquas, which are mixed with animal feeds for feeding animals.

The animal is a livestock, poultry, aquaculture animal or pet.

Specifically, the livestock includes, but is not limited to, a pig, cattle, sheep, horse, rabbit, mink, and the like at various growth stages. The poultry includes, but is not limited to, a chicken, duck, goose, pigeon, and the like at various growth stages. The aquaculture animal includes, but is not limited to, a fish, shrimp, crab, amyda, eel, and the like at various growth stages. And, the pet includes, but is not limited to, an artificial feeding dog or cat.

In an embodiment, the farmer feeds porkers with the feed additives comprising the γ-quaternary ammonium butyrate compound and the racemate, the stereoisomer, the geometric isomer, the tautomer, the solvate or the feed acceptable salt thereof along with feeds, which significantly increases the average daily weight gain rate and feed conversion efficiency of the weaned pigs.

In an embodiment, the farmer feeds broilers with the feed additives comprising the γ-quaternary ammonium butyrate compound and the racemate, the stereoisomer, the geometric isomer, the tautomer, the solvate or the feed acceptable salt thereof along with feeds, which significantly reduces the feed conversion ratio of broilers and increases the feed conversion efficiency.

In an embodiment, the farmer feeds puppies with the feed additives comprising the γ-quaternary ammonium butyrate compound and the racemate, the stereoisomer, the geometric isomer, the tautomer, the solvate or the feed acceptable salt thereof along with feeds.

In other feeding embodiments, the farmer feeds animals with the feed composition comprising the γ-quaternary ammonium butyrate compound and the racemate, the stereoisomer, the geometric isomer, the tautomer, the solvate or the feed acceptable salt thereof, which can significantly improve the production performance of the animals.

Optionally, the feed composition is a feed additive premixing agent, feed additive multi-premixing agent, granule or water aqua, which is fed to animals along with feeds.

In an embodiment, the feed composition is a feed additive premixing agent.

In an embodiment, the feed composition is a feed additive multi-premixing agent.

Optionally, the feed composition is a concentrated feed, a formula feed, a multi-premix or a concentrate supplement, which is directly fed to animals as an animal feed.

In an embodiment, the feed composition is a complete formula feed.

The present disclosure will be described in detail hereinafter in combination with specific examples.

The preparation method of the γ-quaternary ammonium butyrate compound is introduced in detail by taking the preparation process of ethyl L-carnitine chloride and benzyl L-carnitine chloride only as examples.

Example 1. Preparation of ethyl (R)-3-hydroxy-4-(trimethylammonium) butyrate bromide (abbreviated as ethyl L-carnitine bromide)

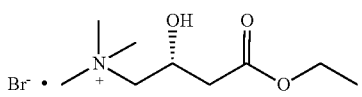

400 g of L-carnitine was weighed into a 2000 ml three-necked flask, 500 ml of acetonitrile was added, the mixture was stirred fully. Then a reflux tube and a drying tube were added, and oil bath was heated to 40° C., then 450 g of bromoethane was added dropwise, and the mixture was stirred at 85° C. When it was confirmed that no raw material was present by monitoring by Thin Layer Chromatography (TLC), the reaction mixture was filtered and the filter cake was dried at 70° C. to obtain 590 g of ethyl L-carnitine bromide, with a yield of 88.86%.

Example 2. Preparation of ethyl (R)-3-hydroxy-4-(trimethylammonium)butyrate chloride (abbreviated as benzyl L-carnitine chloride)

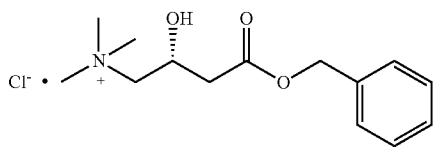

400 g of L-carnitine was weighed into a 3000 ml three-necked flask, 1000 ml of acetonitrile was added, the mixture was stirred fully. Then a reflux tube and a drying tube were added, and oil bath was heated to 70° C., then 400 g of benzyl chloride was added dropwise, and the mixture was stirred at 90° C. When it was confirmed that no raw material was present by monitoring by Thin Layer Chromatography (TLC), the reaction mixture was filtered, and a filter cake was washed with ethanol and dried at 85° C. to obtain 610 g of benzyl L-carnitine chloride as a white solid, with a yield of 86.16%.

Breeding Test

Example 3. Effect of the γ-Quaternary Ammonium Butyrate Compound on the Production Performance of Porkers 90 head of "duroc×landrace×Large Yorkshire" three-way cross lean-type pigs with similar weights having an average weight of 80 kg were randomly divided into 3 treatment groups, each group having 3 repetitions, and each repetition having 10 pigs, half male and half female. The pigsty and appliances were sterilized before testing. During the test, the piglets were fed in separate pigpens under the same feeding and management condition in the same pigsty. During the test, the test pigs ate and drank freely, and were fed twice a day. Each test group is a control group (Group I) and test groups II to III, respectively. Wherein, the control group was fed with a basal diet only, and the test groups II to III were fed with diets that were supplemented with 1000 ppm of different γ-quaternary ammonium butyrate compounds on the basis of the basal diet, specifically as shown in Table 1.

During the entire feeding process, no additional antioxidant components or growth promoters were added for each test group. The test period is 28 days, with each repetition as a unit, the pigs were weighed on the $28^{th}$ day of the test after not stopping water but stopping feeding for 12 hours to calculate the average daily feed intake (ADFI, g/d*head), average daily gain (ADG, g/d*head) and feed conversion ratio (FCR) for each test group. The calculation formulas are as follows:

Average daily feed intake=(total amount of feeds-remaining amount of feeds)/(test days×number of pigs per repetition);

Average daily gain=(average weight at the end of the test-average weight at the beginning of the test)/test days;

Feed conversion ratio=average daily feed intake/average daily gain.

The test results are shown in Table 1 below.

TABLE 1

Results of the effects of the γ-quaternary ammonium butyrate compounds on the production performance of porkers

| Test group | Test sample | ADFI (g/d * head) | ADG (g/d * head) | FCR |
|---|---|---|---|---|
| Group I | — | 2679 | 730 | 3.67 |
| Group II | ethyl L-carnitine bromide | 2624 | 788 | 3.33 |
| Group III | benzyl L-carnitine chloride | 2560 | 790 | 3.24 |

It can be seen from the results in Table 1 that, in this experiment, the effects of the test products on the production performance of the test pigs were compared and assessed from three aspects: feed intake, weight gain and feed conversion efficiency.

Specifically, the γ-quaternary ammonium butyrate compounds involved had no significant effects on the feed intake of each test group; the average daily gain of the test pigs for each test group was increased, compared with the control group; and the feed conversion ratio of each test group was relatively reduced by about 11.72% to 9.26%.

It can be seen that the γ-quaternary ammonium butyrate compounds provided by the present disclosure can effectively improve the growth performance of porkers.

Example 4. Effect of the γ-Quaternary Ammonium Butyrate Compound on the Production Performance of Broilers A single-factor random design was adopted for the test. 360 of one-day-old Chinese three-yellow-feather broilers with similar weights having an average weight of 50 g were randomly divided into 3 treatment groups, each group having 6 repetitions, half male and half female, and each repetition having 20 Chinese three-yellow-feather broilers. The henhouse and appliances were sterilized before testing. During the test, the cage rearing was carried out in the same henhouse under the same feeding and management condition. The basal diet is mainly a corn-soybean meal, and no additional antioxidant components or growth promoters were added during the entire feeding process. Each test group is a control group (Group I) and test groups II to III, respectively. Wherein, the control group was fed with the basal diet only, and the test groups II to III were fed with basal diets that were added with 600 ppm of different γ-quaternary ammonium butyrate compounds. The grouping is shown in Table 2.

The test period was 20 days in total. The test broilers were free to drink and eat, and were fed twice a day. With each repetition as a unit, the test broilers were weighed at the age of 21 days (stopping feeding for 12 hours, without stopping water) to count the consumption of the test broilers, calculate the average daily feed intake (ADFI, g/d*number of broilers), average daily gain (ADG, g/d*number of broilers) and feed conversion ratio (FCR) of each group of test broilers. The calculation formulas are as follows:

Feed conversion ratio (FCR)=average daily feed intake/average daily gain.

The test results are shown in Table 2 below.

TABLE 2

Study effects of the γ-quaternary ammonium butyrate compounds on broiler feeds

| Test group | Test sample | ADFI (g/d * number of broilers) | ADG (g/d * number of broilers) | FCR |
|---|---|---|---|---|
| Group I | — | 32.65 | 12.75 | 2.56 |
| Group II | ethyl L-carnitine bromide | 31.34 | 13.00 | 2.41 |
| Group III | benzyl L-carnitine chloride | 32.18 | 13.46 | 2.39 |

It can be seen from the results in Table 3 that, the test samples have no effect on the feed intake of the test broilers. It can be seen from the average daily gain and feed conversion ratio of each test group that, compared with the control group, the test group added with the γ-quaternary ammonium butyrate compound provided by the present disclosure has a significant improvement effect on the weight gain and feed conversion ratio of the test broilers, and the feed conversion ratio is reduced by 5.86% to 6.64%.

It can be seen that the γ-quaternary ammonium butyrate compound provided by the present disclosure can effectively improve the growth performance of broilers.

Each of the technical features of the above-mentioned embodiments may be combined arbitrarily. To simplify the description, not all the possible combinations of each technical feature in the above embodiments are described. However, all of the combinations of these technical features should be considered as within the scope of the present disclosure, as long as such combinations do not contradict with each other.

The above-mentioned embodiments are merely illustrative of several embodiments of the present disclosure, which are described specifically and in detail, but it cannot be understood to limit the scope of the present disclosure. It should be noted that, for those ordinary skilled in the art, several variations and improvements may be made without departing from the concept of the present disclosure, and all of which are within the protection scope of the present disclosure. Therefore, the protection scope of the present disclosure shall be defined by the appended claims.

What is claimed is:

1. A method of improving animal production performance, the method comprising administering an animal feed additive to an animal, wherein the animal is selected from livestock and poultry; wherein the improved production performance of the animal is improved weight gain or feed conversion efficiency compared to an animal not administered with the animal feed additive, and wherein the animal feed additive comprises a γ-quaternary ammonium butyrate compound having Formula (I), or a racemate, a stereoisomer, a geometric isomer, a tautomer, a solvate or a feed acceptable salt thereof, Formula (I)

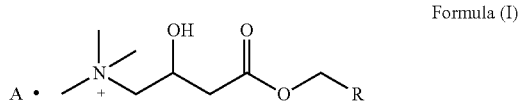

wherein A is an anion; R is $C_1$-$C_{20}$ alkyl, $C_6$-$C_{12}$ aryl, $C_4$-$C_{12}$ heteroaryl, ($C_1$-$C_4$ alkylene)-$C_6$-$C_{12}$ aryl, or ($C_1$-$C_4$ alkylene)-$C_4$-$C_{12}$ heteroaryl, wherein $C_1$-$C_{20}$ alkyl is optionally substituted with one, two, three, four, or five $R^3$, and wherein each of $C_6$-$C_{12}$ aryl, $C_4$-$C_{12}$ heteroaryl, ($C_1$-$C_4$ alkylene)-$C_6$-$C_{12}$ aryl, and ($C_1$-$C_4$ alkylene)-$C_4$-$C_{12}$ heteroaryl is optionally substituted with one, two, three, four, or five $R^4$;

$R^3$ is —OH, —NH$_2$, —CN, —SH or —X$_1$, wherein X$_1$ is F, Cl, Br or I; and $R^4$ is —OH, —NH$_2$, —NO$_2$, —CN, —SH, —X$_2$, —$C_1$-$C_5$ alkoxy, —$C_1$-$C_5$ alkyl, or —$C_1$-$C_5$ alkyl substituted with X$_2$, wherein X$_2$ is F, Cl, Br or I.

2. The method of claim 1, wherein R is $C_1$-$C_{20}$ alkyl or $C_1$-$C_{20}$ alkyl substituted with one, two, three, four, or five $R^3$.

3. The method of claim 2, wherein R is $C_1$-$C_{11}$ alkyl or $C_1$-$C_{11}$ alkyl substituted with one, two, three, four, or five $R^3$.

4. The method of claim 3, wherein R is $C_1$-$C_{11}$ alkyl.

5. The method of claim 4, wherein R is a linear $C_1$-$C_{11}$ alkyl.

6. The method of claim 5, wherein R is $C_1$-$C_3$ alkyl.

7. The method of claim 1, wherein R is $C_6$-$C_{12}$ aryl, or $C_4$-$C_{12}$ heteroaryl, or ($C_1$-$C_4$ alkylene)-$C_6$-$C_{12}$ aryl, or ($C_1$-$C_4$ alkylene)-$C_4$-$C_{12}$ heteroaryl, wherein each of $C_6$-$C_{12}$ aryl, $C_4$-$C_{12}$ heteroaryl, ($C_1$-$C_4$ alkylene)-$C_6$-$C_{12}$ aryl, and ($C_1$-$C_4$ alkylene)-$C_4$-$C_{12}$ heteroaryl is optionally substituted with one, two, three, four, or five $R^4$.

8. The method of claim 7, wherein R is $C_6$-$C_{12}$ aryl or ($C_1$-$C_4$ alkylene)-$C_6$-$C_{12}$ aryl, wherein each of $C_6$-$C_{12}$ aryl and ($C_1$-$C_4$ alkylene)-$C_6$-$C_{12}$ aryl is optionally substituted with one, two, three, four, or five $R^4$.

9. The method of claim 8, wherein R is phenyl or ($C_1$-$C_4$ alkylene) phenyl, wherein each of phenyl and ($C_1$-$C_4$ alkylene) phenyl is optionally substituted with one, two, three, four, or five $R^4$.

10. The method of claim 1, wherein the γ-quaternary ammonium butyrate compound has a structural formula of

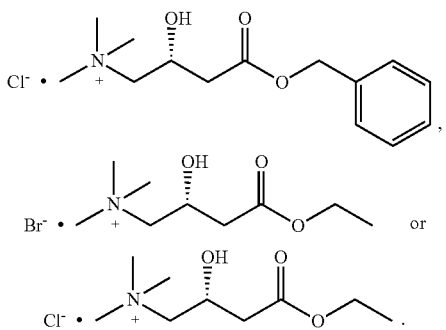

11. The method of claim 1, wherein the γ-quaternary ammonium butyrate compound having Formula (I), or the racemate, the stereoisomer, the geometric isomer, the tautomer, the solvate or the feed acceptable salt thereof is used in combination with at least one additional animal feed additive.

12. The method of claim 11, wherein the at least one additional animal feed additive is selected from at least one of a nutritive feed additive, a non-nutritive feed additive, and a medicated feed additive.

13. The method of claim 1, wherein the γ-quaternary ammonium butyrate compound having Formula (I), or the racemate, the stereoisomer, the geometric isomer, the tautomer, the solvate or the feed acceptable salt thereof is used in combination with at least one animal feed material.

14. The method of claim 11, wherein the γ-quaternary ammonium butyrate compound has a structural formula of
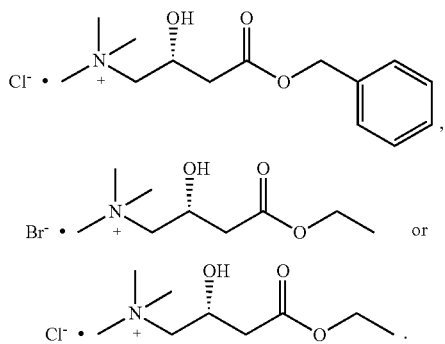
or
15. The method of claim 13, wherein the T-quaternary ammonium butyrate compound has a structural formula of
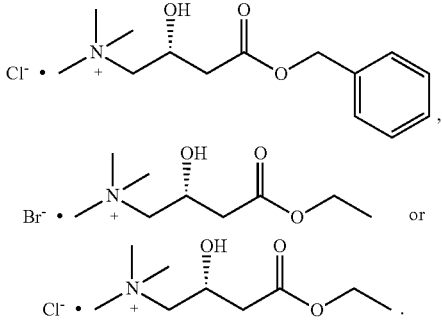
or
* * * * *